United States Patent [19]

Khara

[11] Patent Number: 5,039,639

[45] Date of Patent: Aug. 13, 1991

[54] PROCESS FOR CONVERTING SPENT BUTANE ISOMERIZATION CATALYSTS TO PENTANE ISOMERIZATION CATALYSTS

[75] Inventor: Gyanesh P. Khara, Bartlesville, Okla.

[73] Assignee: Phillips Petroleum Company, Bartlesville, Okla.

[21] Appl. No.: 593,457

[22] Filed: Oct. 5, 1990

[51] Int. Cl.$^5$ .............................................. B01J 38/46
[52] U.S. Cl. ...................................... 502/36; 502/230
[58] Field of Search .................................. 502/36, 230

[56] References Cited

U.S. PATENT DOCUMENTS

| | | | |
|---|---|---|---|
| 3,449,264 | 6/1969 | Myers | 252/441 |
| 3,969,267 | 7/1976 | McVicker | 502/36 |
| 4,014,948 | 3/1977 | Myers | 260/666 P |
| 4,069,268 | 1/1978 | Siskin et al. | 502/36 |
| 4,612,293 | 9/1986 | Johnson | 502/28 |
| 4,644,090 | 2/1987 | Johnson | 585/749 |

OTHER PUBLICATIONS

"Catalyst Manufacture" by Alvin B. Stiles, p. 58, Marcel Dekker, Inc., 1983.

Primary Examiner—Patrick P. Garvin
Assistant Examiner—Brent M. Pebbles
Attorney, Agent, or Firm—K. K. Brandes

[57] ABSTRACT

A spent butane isomerization catalyst comprising platinum and chlorine or alumina is converted in an active n-pentane isomerization catalyst by a process comprising calcining and subsequent heating with a fluorocarbon and/or chlorofluorocarbon. The thus prepared catalyst can be used in the isomerization of n-pentane to isopentane.

19 Claims, No Drawings

PROCESS FOR CONVERTING SPENT BUTANE ISOMERIZATION CATALYSTS TO PENTANE ISOMERIZATION CATALYSTS

This invention relates to isomerization processes and catalysts therefor. In one aspect, this invention relates to the rejuvenation of spent isomerization catalysts. In another aspect, this invention relates to the conversion of spent butane isomerization catalysts to active pentane isomerization catalysts.

BACKGROUND OF THE INVENTION

Catalysts comprising platinum on alumina are useful for the isomerization of saturated hydrocarbons. These catalysts are subject to deactivation as a result of prolonged usage for a variety of reasons. For example, the physical state of the platinum can change under long term exposure to isomerization conditions. Further, contaminants in the feed over an extended period of time tend to deactivate the catalysts. Moreover, carbonization of the catalyst and/or loss of activating catalyst adjuvants can also cause loss of catalyst isomerization activity.

Typically, "spent" (i.e., substantially deactivated) catalysts are processed to extract, separate and recover the platinum values therefore. The recovered platinum values are then used to prepare fresh catalyst. Such a regeneration process is, however, an expensive operation because of the number of steps involved, the amount of reagents required, etc. A process to readily convert a substantially deactivated isomerization catalyst to a once again active isomerization catalyst would, therefore, be of great benefit to those practicing in the field of hydrocarbon isomerizations.

SUMMARY OF THE INVENTION

It is an object of this invention to produce an active pentane isomerization catalyst from a deactivated butane isomerization catalyst. Another object of this invention is the isomerization of pentanes employing a regenerated butane isomerization catalyst. Other objects and advantages will become apparent from the detailed description of the invention and the appended claims.

In accordance with this invention, a process for converting a substantially deactivated butane isomerization catalyst comprising platinum and chlorine (as chloride) on an alumina support to an active catalyst for isomerizing pentanes comprises the steps of:

calcining said substantially deactivated butane isomerization catalyst (referred hereinafter as spent catalyst) at a temperature in the range of about 500° C. to about 700° C. for a time sufficient to remove a substantial portion of chlorine (and also of carbon deposits) contained in said spent catalyst; and treating the thus-calcined catalyst with at least one gaseous effective fluorinating agent selected from the group consisting of fluorocarbons and chlorofluorocarbons (including mixtures thereof) under such conditions as to introduce fluorine (as fluoride ion) into the calcined catalyst and to obtain a fluorinated catalyst which is active as a catalyst for isomerizing n-pentane (normal pentane).

Also in accordance with this invention there is provided an active pentane isomerization catalyst prepared by the above-described reactivation process.

Further in accordance with this invention, there is provided a process for isomerizing n-pentane to isopentane (2-methylbutane) employing a catalyst which has been prepared by the above-described catalyst reactivation process, wherein a n-pentane containing feed is contacted with the catalyst under effective isomerization conditions.

DETAILED DESCRIPTION OF THE INVENTION

Any substantially deactivated (spent) butane isomerization catalyst which contains Pt, Cl and alumina can be used in step (1) of the process of this invention. Fresh (unused) butane isomerization catalysts which catalyze the conversion of n-butane to isobutanes are well known. They can be prepared by processes described in the patent literature, such as in U.S. Pat. Nos. 3,449,264 and 4,014,948. Butane isomerization catalysts are also commercially available, e.g., from UOP, Inc., Des Plaines, Ill., and from the Catalyst and Chemicals Division of Engelhard Corporation, Newark, N.J. Generally, these catalysts contain about 0.01–10 (preferably about 0.1–1) weight-% Pt and about 1–10 (preferably about 2–6) weight-% Cl. The spent butane isomerization catalyst which is used in step (1) of the reactivation process of this invention is one of the above-described fresh catalyst which has been employed in a butane isomerization process and has become substantially deactivated (to the extent that the catalyst no longer satisfies the required conversion/selectivity requirements for the butane isomerization process). The weight percentages of Pt and Cl in the spent catalyst are essentially the same as those in the fresh catalyst.

The calcining step can be carried out by heating the spent butane isomerization catalyst at about 500°–800° C., preferably at about 600°–750° C., so as to remove a substantial portion (i.e., at least about 50%) of chlorine contained in the spent catalyst. Preferably, also a significant portion of carbon deposits on the spent catalyst (which generally contains 0.05–1.0 weight-% C) is removed during calcining. Preferably, about 50–99% (more preferably about 60–98%) of the chlorine is removed in this calcining step. Generally, this will require a heating time of at least about 5 minutes, and may require up to about 40 hours (especially when heated at a low temperature). Preferably, a heating time of about 10 minutes to about 10 hours, more preferably about 15 minutes to 60 minutes is employed. The calcining step can be carried out in an oxidizing atmosphere (such as air) or in an inert atmosphere (such as $N_2$), preferably in a free oxygen containing gas atmosphere. The calcining operation can be carried out in any of the well known heating vessels, preferably in a rotary calciner. Gaseous HCl is generated during the calcining step and should be removed (preferably by scrubbing with aqueous NaOH) before the exiting gas is released into the atmosphere.

The fluorinating step can be carried out in any suitable manner in any suitable vessel. The calcined spent catalyst is contacted under fluorinating conditions with gaseous fluorocarbon(s) and/or chlorofluorocarbon(s) as effective fluorinating agent(s), preferably at a temperature of about 250° to about 650° C. Non-limiting examples of effective fluorocarbons are: $CH_3F$, $CH_2F_2$, $CHF_3$, $CF_4$, $CH_3CH_2F$, $CH_3CHF_2$, $CH_2FCHF_2$, $CH_3CF_3$, $CH_2FCF_3$, $CHF_2CHF_2$, $CHF_2CF_3$, $CF_3CF_3$, $CF_3CF_2CF_3$, and the like, and mixtures thereof. Non-limiting examples of effective chlorofluorocarbons are:

$CH_2ClF$, $CHCl_2F$, $CHClF_2$, $CCl_2F_2$, $CClF_3$, $CH_3CClF_2$, $CH_2ClCF_3$, $CHF_2CClF_2$, $CClF_2CClF_2$, $CCl_2FCF_3$, $CClF_2CF_3$, and the like, and mixtures thereof. Also mixtures of fluorocarbons and chlorofluorocarbons can be employed. Many of the above-cited fluorocarbons and chlorofluorocarbons are commercially available as refrigerants, e.g., $CCl_2F_2$ (Freon 12), $CClF_3$ (Freon 13), $CF_4$ (Freon 14), $CHClF_2$ (Freon 22) and $CHF_3$ (Freon 23).

During the fluorinating step, the gaseous fluorinating agent is generally diluted with an inert gas (e.g., $N_2$, He, or Ar) or with a free oxygen containing gas, preferably air (so as to convert excess fluorinating agent to carbon oxides). Generally, the concentration of the fluorocarbon(s) and/or chlorofluorocarbon(s) in such gas mixtures is about 2 to about 50 volume-%, more preferably about 10-30 volume-%. The contacting of the calcined spent catalyst with the fluoroinating agent at about 250°-600° C. (more preferably about 280°-500° C.) is carried out for a period of time sufficient to incorporate a desired amount of fluorine into the catalyst. Depending on the contacting temperature and the concentration of the fluorinating agent in the gas phase, the contact time generally ranges from about 1 minute to about 2 hours (preferably about 0.1-1 hour). The fluorinating agents of this invention are substantially non-corrosive at the contacting conditions.

The final catalyst composition, which has been prepared by the catalyst reactivation process of this invention and which is active as a pentane isomerization catalyst, generally contains about 0.01-10 weight-% Pt (preferably about 0.1-1 weight-% Pt), about 0.1-12 weight-% F (preferably about 0.3-5 weight-% F) and about 0.01-4 weight-% Cl (preferably about 0.02-2 weight-% Cl). The final catalyst may also contain small amounts of carbon (preferably less than about 0.1 weight percent). When the chlorine content of the final catalyst composition is higher than desired, the catalyst can be washed with an aqueous liquid, preferably water (so as to wash out excess chloride), and then dried (preferably at about 80°-200° C. for about 0.5-5 hours).

In accordance with a particular embodiment of the present invention, a process for the isomerization of n-pentane to isopentanes is provided employing the fluoride-containing platinum on alumina isomerization catalyst prepared as described therein above. Thus, a pentane-containing feed is typically contacted with the substantially water-free fluoride-containing platinum on alumina isomerization catalyst in a plug flow fixed bed reactor. Preferably, the catalyst is heated in a free hydrogen stream at about 300°-800° F. prior to contacting with the n-pentane containing feed. Process conditions for the pentane isomerization process are well known to those skilled in the art and have been described in the patent literature (e.g., U.S. Pat. No. 4,612,293). Preferred conditions for carrying out the isomerization process of the present invention include a temperature of about 500°-800° F. (more preferably about 650°-720° F.), a pressure of about 150-1500 psig, a hydrogen to n-pentane feed volume ratio in the range of about 0.5:1 to about 10:1 (more preferably about 1:1 to about 3:1), and a liquid hourly space velocity of n-pentane in the range of about 0.2 to 6 (more preferably about 1-3) cc feed/cc catalyst/hour. Isopentane can be separated from unconverted n-pentane and by-products by conventional means.

The following examples are presented to further illustrate the invention and are not to be considered as unduly limiting the scope of the invention.

EXAMPLE

This example illustrates the rejuvenation of a spen "I-8" butane isomerization catalyst (1/16" extrudates) in accordance with this invention.

The fresh "I-8" catalyst had been purchased from UOP, Inc., Des Plains, Ill., and had then been used in a commercial n-butane isomerization unit of Phillips Petroleum Company at its Borger, Tex., refinery until the catalyst had become substantially inactive. The spent "I-8" catalyst contained about 0.2 weight-% Pt, about 3.4 weight-% Cl and about 0.12 weight-% C, and exhibited a grey color.

Spent catalyst samples (50–100 g) were first calcined in a stream of air at about 650° C. for about one hour. Thereafter, the calcined samples were contacted at various temperatures and at atmospheric pressure conditions with a mixture of air and a fluorocarbon or a chlorofluorocarbon for about 8–60 minutes (depending on the fluorinating temperature, the employed fluorinating agent and the desired fluorine content in the treated catalyst). The fluorination treatment was generally stopped when there was either no evolution of water vapor or when the temperature increase from the start temperature had ceased. The fluorinated spent catalysts were analyzed for F and Cl. Fluorination conditions and results are summarized in Table I.

TABLE I

| Run | Employed Freon[1] | Fluorination Temp. (°F.) | Freon Feed Rate[2] (cc/min) | Chemical Analysis Wt-% F | Wt-Cl |
|---|---|---|---|---|---|
| 1 | F-23 | 550 | 23 | 0.80 | 1.53 |
| 2 | F-23 | 550 | 240 | 2.76 | 0.52 |
| 3 | F-23 | 550 | 804 | 10.7 | 0.21 |
| 4 | F-23 | 950 | 21 | 1.14 | 1.16 |
| 5 | F-14 | 550 | 86 | 0.01 | 1.39 |
| 6 | F-14 | 650 | 63 | 0.03 | 1.61 |
| 7 | F-14 | 750 | 13 | 1.28 | 1.26 |
| 8[3] | F-12 | 550 | 65 | 0.37 | 2.41 |
| 9[3] | F-12 | 550 | 51 | 3.52 | 1.93 |
| 10[3] | F-12 | 750 | 62 | 2.50 | 2.60 |
| 11[3] | F-12 | 950 | 54 | 3.27 | 2.05 |

[1] F-23 = fluoroform ($CHF_3$); F-14 = tetrafluoromethane ($CF_4$); F-12 = difluorodichloromethane ($CF_2Cl_2$);
[2] 1000 cc/min of air was employed as diluent in each experiment;
[3] these runs used 50 g catalyst in a stainless steel reactor of 18 inches length and 1 inch diameter; all other runs used 100 g catalyst in a quartz reactor of 18 inches length and 1.5 inch diameter.

Test results shown in Table I clearly demonstrate the effectiveness of Freons to fluorinate the spent I-8 catalyst. It is also evident that different fluorinating temperatures were required for different fluorocarbons. Fluoroform (F-23) appeared to be most reactive and effected fluorination at a lower temperature than, for example, $CF_4$ (F-14) which appeared to be the least reactive since it required higher reaction temperature for fluorination. A desired amount of fluoride could be incorporated into the catalyst by controlling the feed concentration of a Freon. When difluorodichloromethane (Freon 12) was used, the chloride content of the catalyst also increased, which is believed to be detrimental in that it may cause downstream corrosion problems in a refinery. By washing high chloride samples with hot water, the chloride content can be reduced.

EXAMPLE II

The fluorinated spent catalyst of Run 9 (see Table I) was tested for its catalytic performance in a n-pentane isomerization reaction, substantially in accordance with the procedure described in Example II of U.S. Pat. No. 4,612,293. Samples of 22 cc of the rejuvenated catalyst were placed into a tubular, heated stainless steel reactor (½ inch diameter) and were pretreated (activated) for several hours in a stream of hydrogen (flow rate: 400-600 cc/minute), at a temperature slowly rising from about 300°-400° F. to about 700°-750° F. under atmospheric pressure conditions. Then liquid n-pentane was introduced at the top of the reactor and was pumped through the catalyst bed at a liquid hourly space velocity of 2.0 cc/cc catalyst/hour. The reactor was pressurized with hydrogen gas to an operating pressure of 480 psig. To maintain this pressure, the flow rate of approximately 25 liters of $H_2$ per hour was required. Test results are summarized in Table II.

TABLE II

| Run | Isomeriz. Temp. (°F.) | Effluent Composition (Wt-%) | | | | $iC_5/nC_5$ Ratio[4] |
|---|---|---|---|---|---|---|
| | | Isopentane | n-Pentane[1] | Lights[2] | Heavies[3] | |
| 12 | 728 | 58.6 | 31.3 | 8.8 | 1.3 | 1.87 |
| 13 | 728 | 58.5 | 31.4 | 8.9 | 1.3 | 1.86 |
| 14 | 664 | 47.9 | 51.0 | 0.5 | 0.6 | 0.94 |
| 15 | 683 | 55.2 | 43.5 | 0.7 | 0.6 | 1.27 |
| 16 | 703 | 60.8 | 37.6 | 1.1 | 0.5 | 1.62 |
| 17 | 703 | 61.4 | 36.7 | 1.6 | 0.5 | 1.67 |
| Control[5] | 754 | 14 | — | — | — | — |
| Control[5] | 719 | 7 | — | — | — | — |

[1] unconverted n-pentane feed
[2] cracked hydrocarbon products containing less than 5 C atoms per molecules
[3] oligomerized hydrocarbon products contained more than 5 C atoms per molecule
[4] ratio of formed isopentane to unconverted n-pentane
[5] employing rejuvenated catalyst in accordance with U.S. Pat. No. 4,612,293

Test data in Table II clearly demonstrate that a fluorinated spent I-8 catalyst, prepared by the rejuvenation method of this invention, was considerably more effective as catalyst for converting n-pentane to isopentane than a control catalyst which had been rejuvenated by the method disclosed in U.S. Pat. No. 4,612,293 (comprising washing, fluorination with HF, and drying). Test data in Table II also indicate that a temperature of about 680-700 is most preferred, in order to attain a desirable combination of high isobutane yield and low yield of lights (cracked products).

Reasonable variations, modifications and adaptations for various usages and conditions can be made within the scope of the disclosure and the appended claims, without departing from the scope of this invention.

That which is claimed is:

1. A process for converting a spent butane isomerization catalyst which comprises platinum and chlorine on an alumina support to an active catalyst for isomerizing pentanes comprising the steps of:
   calcining said spent butane isomerization catalyst at a temperature in the range of about 500° C. to about 700° C. for a time sufficient to remove a substantial portion of chlorine contained in said spent catalyst; and
   treating the thus-calcined catalyst with at least one gaseous effective fluorinating agent selected from the group consisting of fluorocarbons and chlorofluorocarbons under such conditions as to introduce fluorine into the calcined catalyst and to obtain a fluorinated catalyst which is active as a catalyst for isomerizing n-pentane.

2. A process in accordance with claim 1, wherein said spent catalyst comprises about 0.01-10 weight percent platinum, about 1-10 weight percent chlorine, and about 0.05-1.0 weight percent carbon.

3. A process in accordance with claim 1, wherein said calcining is carried out in a free oxygen containing gas atmosphere at a temperature of about 600°-750° C. for about 10 minutes to about 10 hours.

4. A process in accordance with claim 1, wherein said at least one gaseous effective fluorinating agent is selected from the group consisting of $CH_3F$, $CH_2F_2$, $CHF_3$, $CF_4$, $CH_3CH_2F$, $CH_3CHF_2$, $CH_2FCHF_2$, $CH_3CF_3$, $CH_2FCF_3$, $CHF_2CHF_2$, $CHF_2CF_3$, $CF_3CF_3$, $CF_3CF_2CF_3$, $CH_2ClF$, $CHCl_2F$, $CHClF_2$, $CCl_2F_2$, $CClF_3$, $CH_3CClF_2$, $CH_2ClCF_3$, $CHF_2CClF_2CClF_2$, $CCl_2FCF_3$, $CClF_2CF_3$, and mixtures thereof.

5. A process in accordance with claim 4, wherein said fluorinating agent is selected from the group consisting of $CCl_2F_2$, $CClF_3$, $CF_4$, $CHClF_2$, $CHF_3$, and mixtures thereof.

6. A process in accordance with claim 1, wherein said treating with at least one gaseous effective fluorinating agent is carried out at a temperature of about 250°-600° C. for about 1 minute to about 2 hours.

7. A process in accordance with claim 1 comprising the additional steps of washing said fluorinated catalyst with an aqueous liquid and thereafter drying the washed catalyst.

8. A process in accordance with claim 1, wherein said fluorinated catalyst comprises about 0.01-10 weight-percent Pt, about 0.1-12 weight percent F and about 0.01-4 weight percent Cl.

9. A process in accordance with claim 8, wherein said fluorinated catalyst comprises about 0.1-1 weight percent Pt, about 0.3-5 weight percent F and about 0.02-2 weight percent Cl.

10. A process for converting a spent butane isomerization catalyst which comprises platinum and chlorine on an alumina support to an active catalyst for isomerizing pentanes comprising the steps of:
   calcining said spent butane isomerization catalyst at a temperature in the range of about 500° C. to about 700° C. for a time sufficient to remove a substantial portion of chlorine contained in said spent catalyst; and
   treating the thus-calcined catalyst with at least one gaseous effective fluorinating agent selected from the group consisting of fluorocarbons and chlorofluorocarbons under such conditions as to introduce fluorine into the calcined catalyst and to obtain a fluorinated catalyst which is active as a catalyst for isomerizing n-pentane;
   wherein said at least one gaseous fluorinating agent is admixed with a free oxygen-containing gas.

11. A process in accordance with claim 10, wherein said spent catalyst comprises about 0.01-10 weight percent platinum, about 1-10 weight percent chlorine, and about 0.05-1.0 weight percent carbon.

12. A process in accordance with claim 10, wherein said calcining is carried out in a free oxygen containing gas atmosphere at a temperature of about 600°-750° C. for about 10 minutes to about 10 hours.

13. A process in accordance with claim 10, wherein said at least one gaseous effective fluorinating agent is selected from the group consisting of $CH_3F$, $CH_2F_2$, $CHF_3$, $CF_4$, $CH_3CH_2F$, $CH_3CHF_2$, $CH_2FCHF_2$, $CH_3CF_3$, $CH_2FCF_3$, $CHF_2CHF_2$, $CHF_2CF_3$, $CF_3CF_3$, $CF_3CF_2CF_3$, $CH_2ClF$, $CHCl_2F$, $CHClF_2$, $CCl_2F_2$, $CClF_3$, $CH_3CClF_2$, $CH_2ClCF_3$, $CHF_2CClF_2$, $CClF_2CClF_2$, $CCl_2FCF_3$, $CClF_2CF_3$, and mixtures thereof.

14. A process in accordance with claim 13, wherein said fluorinating agent is selected from the group consisting of $CCl_2F_2$, $CClF_3$, $CF_4$, $CHClF_2$, $CHF_3$, and mixtures thereof.

15. A process in accordance with claim 10, wherein said treating with at least one gaseous effective fluorinating agent is carried out at a temperature of about 250°–600° C. for about 1 minute to about 2 hours.

16. A process in accordance with claim 10, comprising the additional steps of washing said fluorinated catalyst with an aqueous liquid and thereafter drying the washed catalyst.

17. A process in accordance with claim 10, wherein said fluorinated catalyst comprises about 0.01–10 weight-percent Pt, about 0.1–12 weight percent F and about 0.01–4 weight percent Cl.

18. A process in accordance with claim 12, wherein said fluorinated catalyst comprises about 0.1–1 weight percent Pt, about 0.3–5 weight percent F and about 0.02–2 weight percent Cl.

19. A process in accordance with claim 10, wherein the volume percentage of said at least one gaseous effective fluorinating agent in the mixture with said free oxygen-containing gas is about 2–50 volume-%.

* * * * *

UNITED STATES PATENT AND TRADEMARK OFFICE
CERTIFICATE OF CORRECTION

PATENT NO.  : 5,039,639

DATED       : August 13, 1991

INVENTOR(S) : Gyanesh P. Khare

It is certified that error appears in the above-identified patent and that said Letters Patent is hereby corrected as shown below:

Title page, left column, item [75], delete "Khara" and substitute --- Khare --- therefor.

Signed and Sealed this

Ninth Day of February, 1993

Attest:

STEPHEN G. KUNIN

*Attesting Officer*  Acting Commissioner of Patents and Trademarks